(12) United States Patent
Akahori et al.

(10) Patent No.: US 9,661,999 B2
(45) Date of Patent: May 30, 2017

(54) ENDOSCOPE REPROCESSOR (71) Applicant: OLYMPUS CORPORATION, Tokyo (JP)

(72) Inventors: Hiromasa Akahori, Tachikawa (JP); Hideto Onishi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/274,397

(22) Filed: Sep. 23, 2016

(65) Prior Publication Data
US 2017/0007108 A1 Jan. 12, 2017

Related U.S. Application Data (63) Continuation of application No. PCT/JP2015/077548, filed on Sep. 29, 2015.

(30) Foreign Application Priority Data

Nov. 17, 2014 (JP) .................................. 2014-232938

(51) Int. Cl.
*A61L 2/00* (2006.01)
*A61B 1/00* (2006.01)
(Continued)

(52) U.S. Cl.
CPC ................. *A61B 1/123* (2013.01); *A61B 1/12* (2013.01); *A61B 1/125* (2013.01); *A61L 2/18* (2013.01);
(Continued)

(58) Field of Classification Search
CPC .............. A61B 1/125; B08B 3/04; A61L 2/18
(Continued)

(56) References Cited

U.S. PATENT DOCUMENTS

2008/0267812 A1* 10/2008 Kawachi .................. A61L 2/18
422/3

FOREIGN PATENT DOCUMENTS

JP          61-40556 A      2/1986
JP       2009-216523 A      9/2009
(Continued)

OTHER PUBLICATIONS

International Search Report dated Oct. 27, 2015 issued in PCT/JP2015/077548.
(Continued)

*Primary Examiner* — Monzer R Chorbaji
(74) *Attorney, Agent, or Firm* — Scully, Scott, Murphy & Presser, P.C.

(57) ABSTRACT

An endoscope reprocessor of the present invention includes a reservoir configured to store a solution, a fluid supply section configured to supply the solution into the reservoir, a fluid discharge section configured to discharge the solution from the reservoir, a recessed pool section fixed inside the reservoir and having a bottom surface positioned below an opening section in a gravitational direction, and a concentration meter including a permeable membrane having a first surface exposed inside the pool section, at least a part of the first surface being positioned below the opening section in the gravitational direction, an accommodation section having a container shape and including a part of a second surface of the permeable membrane as an inner surface, the second surface being on an opposite side to the first surface, internal liquid accommodated in the accommodation section, and an electrode accommodated in the accommodation section.

2 Claims, 11 Drawing Sheets (51) Int. Cl.
    *B08B 3/00*     (2006.01)
    *A61B 1/12*     (2006.01)
    *A61L 2/18*     (2006.01)
    *A61L 2/26*     (2006.01)
    *A61B 90/70*     (2016.01)

(52) U.S. Cl.
    CPC ........... *A61L 2/26* (2013.01); *A61B 2090/701* (2016.02); *A61L 2202/14* (2013.01); *A61L 2202/17* (2013.01); *A61L 2202/24* (2013.01)

(58) Field of Classification Search
    USPC ....... 422/292, 300; 134/108, 166 R; 600/133
    See application file for complete search history.

(56) References Cited

FOREIGN PATENT DOCUMENTS

| | | |
|---|---|---|
| JP | 2010-57793 A | 3/2010 |
| JP | 2014-100313 A | 6/2014 |

OTHER PUBLICATIONS

Japanese Office Action dated Mar. 15, 2016 issued in JP 2015-556889.

\* cited by examiner

ENDOSCOPE REPROCESSOR

CROSS REFERENCE TO RELATED APPLICATION

This application is a continuation application of PCT/JP2015/077548 filed on Sep. 29, 2015 and claims benefit of Japanese Application No. 2014-232938 filed in Japan on Nov. 17, 2014, the entire contents of which are incorporated herein by this reference.

BACKGROUND OF THE INVENTION

1. Field of the Invention

The present invention relates to an endoscope reprocessor provided with a concentration meter which is configured to measure the concentration of a solution.

2. Description of the Related Art

Endoscopes used in the medical field are subjected to a cleaning process and a disinfecting process after use. Also, endoscope cleaning/disinfecting apparatuses configured to automatically perform the cleaning process and the disinfecting process on the endoscopes are known. In the case of providing to the endoscope cleaning/disinfecting apparatus a function for automatically determining whether a solution such as a disinfecting solution may be used or not, a concentration meter which is configured to measure the concentration of a solution becomes necessary.

As the concentration meter, there is known a type that uses an electrode and a permeable membrane that selectively allows a specific gas or ion to pass through, as disclosed in Japanese Patent Application Laid-Open Publication No. 2009-216523, for example. In the case of measuring the concentration of a solution by using this type of concentration meter, a sensor section, which is the part where the permeable membrane is provided, is immersed in the solution.

SUMMARY OF THE INVENTION

An endoscope reprocessor according to an aspect of the present invention includes a reservoir configured to store a solution; a fluid supply section configured to supply the solution into the reservoir; a fluid discharge section configured to discharge the solution from the reservoir; a recessed pool section that is fixed inside the reservoir and having a bottom surface positioned below an opening section in a gravitational direction; and a concentration meter including a permeable membrane having a first surface exposed inside the pool section, at least a part of the first surface being positioned below the opening section in the gravitational direction, an accommodation section having a container shape and including a part of a second surface of the permeable membrane as an inner surface, the second surface being on an opposite side to the first surface, internal liquid that is accommodated in the accommodation section, and an electrode that is accommodated in the accommodation section.

DETAILED DESCRIPTION OF THE PREFERRED EMBODIMENT(S)

Hereinafter, preferred embodiments of the present invention will be described with reference to the drawings. Note that, in each of the drawings used in the following description, the scale of each component is made different such that each component is large enough to be recognized in the drawing, but the present invention is not limited to the modes shown in the drawings with respect to the number of components, the shapes of the components, the proportion of the sizes of the components, and the relative positional relationship of the components.

An endoscope reprocessor of the present invention is a device configured to perform a reprocessing process on a contaminated endoscope or endoscopic accessory. The reprocessing process here is not particularly limited, and may be any of rinsing by water, cleaning for washing out contaminants such as organic substances, disinfection for neutralizing certain microbes, sterilization for excluding or destroying all the microbes, and a combination among rinsing, cleaning, disinfection, and sterilization.

First Embodiment

Hereinafter, a first embodiment will be described as an example of an embodiment of the present invention. An endoscope reprocessor 20 shown in FIG. 1 is an apparatus configured to perform a rinsing process and a disinfecting or sterilization process on at least of one of an endoscope and an endoscopic accessory (neither is shown in the drawing) by using water, a drug solution or the like.

Figure 1:
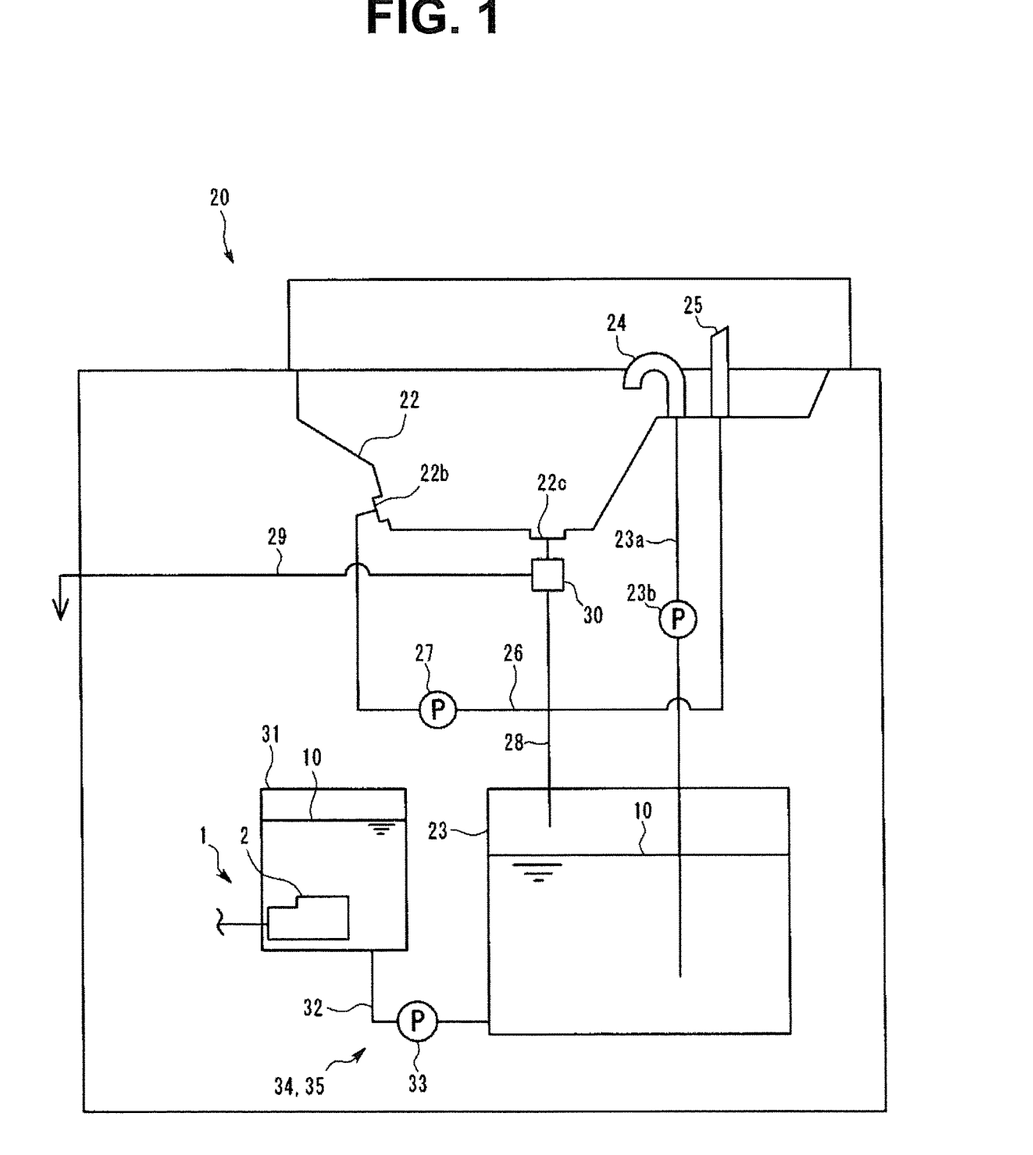
FIG. 1 is a diagram showing a configuration of an endoscope reprocessor of a first embodiment.

As shown in FIG. 1, the endoscope reprocessor 20 is configured by including a processing tank 22, a drug solution tank 23, a reservoir 31, and a concentration meter 1. The processing tank 22 has a recessed shape with an opening section which is opened upward, and is capable of accommodating at least one of an endoscope and an endoscopic accessory. The processing tank 22 is configured to allow storing a liquid inside.

The drug solution tank 23 is a part configured to store a solution 10, which is a drug solution. The drug solution may be used for any of cleaning, disinfection, and sterilization. A peracetic acid solution may be cited as a drug solution for disinfection or sterilization. The drug solution tank 23 is connected via a drug solution introduction channel 23a to a disinfecting solution nozzle 24, which is disposed inside the processing tank 22. A drug solution introduction pump 23b is disposed to the drug solution introduction channel 23a.

The solution 10 that is stored in the drug solution tank 23 is introduced into the processing tank 22 by the action of the drug solution introduction pump 23b.

Furthermore, a circulation nozzle 25 is disposed inside the processing tank 22. A circulation port 22b and a solution discharge port 22c are provided at a lower portion of the processing tank 22. The circulation nozzle 25 communicates with the circulation port 22b through a circulation channel 26.

A circulation pump 27 is provided to the circulation channel 26. Liquid inside the processing tank 22 is sucked out from the circulation port 22b, and is then returned to the processing tank 4 via the circulation channel 26 and the circulation nozzle 25, by the action of the circulation pump 27. The endoscope reprocessor 20 accommodates at least one of the endoscope and an endoscopic accessory in the processing tank 22, and performs a rinsing process, a disinfecting process or the like on at least one of the endoscope and the endoscopic accessory by causing water, a disinfecting solution or the like to circulate.

The solution discharge port 22c is a part configured to discharge liquid that is stored in the processing tank 22 to outside the processing tank 22 by gravity. The solution discharge port 22c is connected to a collection channel 28 and a solution discharge channel 29 via a switching valve 30. The switching valve 30 is capable of switching to a state where the solution discharge port 22c is opened and is connected to one of the collection channel 28 and the solution discharge channel 29, or a state where the solution discharge port 22c is closed.

The collection channel 28 connects the switching valve 30 and the drug solution tank 23 to each other. When the solution discharge port 22c is opened and the solution discharge port 22c and the solution discharge channel 29 are connected in a state where the solution 10, which is a disinfecting solution, is stored in the processing tank 22, the solution 10 in the processing tank 22 is collected in the drug solution tank 23.

The solution discharge channel 29 extends to outside the endoscope reprocessor 20. When the solution discharge port 22c is opened and the solution discharge port 22c and the solution discharge channel 29 are connected to each other, liquid that is stored in the processing tank 22 is discharged outside the endoscope reprocessor 20.

The reservoir 31 is a container configured to store a liquid inside. Also, a sensor section 2 of the concentration meter 1, which is a device configured to measure the concentration of the solution 10, is disposed to the reservoir 31. The reservoir 31 communicates with the drug solution tank 23 via a channel 32. A pump 33 is disposed on the channel 32. The pump 33 is capable of forward/backward operation, and is capable of an operation of transferring the solution 10 in the drug solution tank 23 to the reservoir 31, and an operation of transferring the solution 10 in the reservoir 31 to the drug solution tank 23. That is, the channel 32 and the pump 33 configure a fluid supply section 34 configured to supply the solution 10 to the reservoir 31, and a fluid discharge section 35 configured to discharge the solution 10 from the reservoir 31.

Note that a mode is also possible where one of supply of the solution 10 to the reservoir 31 and discharge of the solution 10 from the reservoir 31 is performed under the action of gravity, without using the pump 33. Also, a mode is possible where the fluid supply section 34 configured to supply the solution 10 to the reservoir 31 and the fluid discharge section 35 configured to discharge the solution 10 from the reservoir 31 have different configurations.

The endoscope reprocessor 20 of the present embodiment is designated such that, all the solution 10 is discharged from the reservoir 31 at the time of performing a rinsing process, a disinfecting process or the like on at least one of an endoscope and an endoscopic accessory inside the processing tank 22.

Moreover, the endoscope reprocessor 20 performs measurement of the concentration of the solution 10 stored in the drug solution tank 23 before performing a disinfecting process or the like on at least one of the endoscope and the endoscopic accessory. When performing measurement of the concentration of the solution 10, the endoscope reprocessor 20 causes a predetermined volume of solution 10 to flow into the reservoir 31 from the drug solution tank 23 by operating the pump 33. The volume of the solution 10 to be transferred to the reservoir 31 takes a value by which the sensor section 2 is immersed into the solution.

After the solution 10 flows into the reservoir 31, the endoscope reprocessor 20 operates the concentration meter 1 and measures the concentration of the solution 10. If the measurement result of the concentration of the solution 10 by the concentration meter 1 is within a range of predetermined values, the endoscope reprocessor 20 determines that the disinfecting process can be performed on at least one of the endoscope and the endoscopic accessory by using the solution 10. On the other hand, if the measurement result of the concentration of the solution 10 by the concentration meter 1 is outside the range of the predetermined values, the endoscope reprocessor 20 determines that the disinfecting process for at least one of the endoscope and the endoscopic accessory using the solution 10 is not possible, and issues an alarm to the user by emitting sound or light, for example.

The concentration meter 1 has a configuration of an electrochemical sensor that uses an ion selective electrode. The concentration meter 1 includes the sensor section 2, shown in FIG. 2, disposed in the reservoir 31. The sensor section 2 includes a well-known configuration called an ion selective electrode, for example. The sensor section 2 includes a main body section 3 where a pool section 9 and a permeable membrane 4 are disposed. The main body section 3 has a fixed position inside the reservoir 31.

The pool section 9 is a recessed concave part which is open toward the space inside the reservoir 31. In the present embodiment shown in FIG. 2, the pool section 9 is opened upward at the uppermost part of the main body section 3, but the arranged position and the opening direction of the pool section 9 are not limited to those of the present embodiment. It is sufficient if the shape of the pool section 9 is such that the bottom surface is lower in the gravitational direction than the lowermost end of an opening section 9a which is open to the outside of the main body section 3. The bottom surface here refers to the part which is at the lowest position, of the inner surfaces of the recessed pool section 9.

Figure 2:
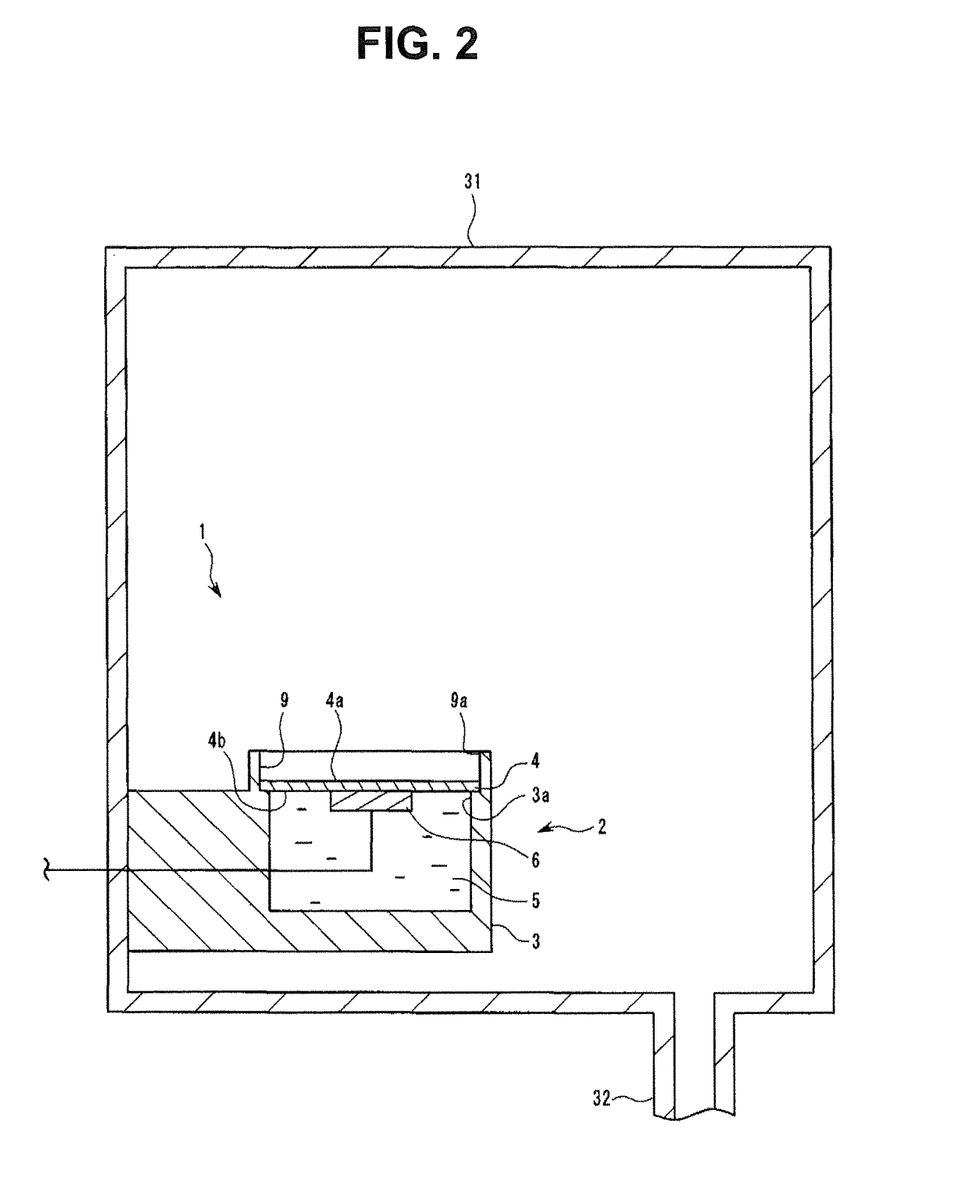
FIG. 2 is a cross-sectional view of a reservoir and a sensor section of a concentration meter of the first embodiment.

In other words, it is sufficient if the pool section 9 is shaped such that the solution 10 flows inside from the opening section 9a when the opening section 9a is sunk into the solution 10, and then, when the opening section 9a is exposed to the air, at least a part of the solution 10 which has flown inside is retained inside. For example, the pool section 9 may be opened at a lateral side surface of the main body section 3, and be recessed in an obliquely downward direction. Note that a plurality of opening sections 9a may be provided.

Inside the main body section 3, an accommodation section 3a, which is a recessed part provided on inner wall surfaces of the pool section 9, is provided. The accommodation section 3a and the pool section 9 are separated by the permeable membrane 4.

The permeable membrane 4 is a part that selectively allows a specific gas or ion to pass through. The permeable membrane 4 is configured by a material that is selected according to the type of solution 10 which is the target of concentration measurement by the concentration meter 1, and is not particularly limited. An internal liquid 5 and an electrode 6 are accommodated inside the accommodation section 3a sealed by the permeable membrane 4. The electrode 6 and the permeable membrane 4 are joined by the internal liquid 5. The term "joined" here refers to a state where a measurement target material which has passed through the permeable membrane 4 and reached the internal liquid 5 is allowed to reach the electrode 6 with the internal liquid 5 as the medium.

In this manner, according to the concentration meter 1 of the present embodiment, at least a part of a first surface 4a, which is one surface of the permeable membrane 4, is exposed inside the pool section 9, and at least a part of a second surface, which is the other surface of the permeable membrane 4, is in contact with the internal liquid 5. That is, at least a part of the first surface 4a of the permeable membrane 4 configures a part of the inner surfaces of the pool section 9, and at least a part of the second surface 4b of the permeable membrane 4 configures a part of the inner surfaces of the accommodation section 3a.

The permeable membrane 4 is disposed in such a way that at least a part of the first surface is immersed in the solution 10 that is retained inside the pool section 9 in a state where the opening section 9a is exposed to the air. In other words, at least a part of the first surface 4a of the permeable membrane 4 is at a position lower than the lowermost end of the opening section 9a.

As an example in the present embodiment, the permeable membrane 4 has the first surface 4a disposed facing upward at the bottom surface of the pool section 9, and the accommodation section 3a is at a position below the permeable membrane 4.

Note that, in the illustrated embodiment, the permeable membrane 4 is planar, but the permeable membrane 4 may have a curved surface, such as a cylindrical surface or a spherical surface. Also, the concentration meter 1 of the present embodiment is provided with one permeable membrane 4 and one accommodation section 3a, but the concentration meter 1 may be provided with a plurality of permeable membranes 4 and a plurality of accommodation sections 3a.

The electrode 6 is electrically connected to a control section, not shown, of the concentration meter 1. The concentration meter 1 includes, in addition to the sensor section 2, a reference electrode, not shown, which is electrically connected to the control section. The position where the reference electrode is disposed is determined according to the measurement principle of the concentration meter 1, and is not particularly limited. The reference electrode may be disposed inside the main body section 3 or outside the main body section 3.

The concentration meter 1 measures, at the control section, a change in the potential difference between the electrode 6 and the reference electrode, or a change in the value of current flowing between the electrodes, and based on the measurement value, measures the concentration of the solution 10 in which the sensor section 2 is immersed. The principle and the configuration for concentration measurement by the concentration meter, which is an electrochemical sensor, are well-known, and detailed description is omitted.

As described above, the endoscope reprocessor 20 of the present embodiment includes, inside the reservoir 31 configured to store the solution 10, the concentration meter 1 including the recessed pool section 9 and the permeable membrane 4 whose first surface 4a is at least partially exposed inside the pool section 9. Also, the endoscope reprocessor 20 includes the fluid supply section 34 configured to supply the solution 10 to the reservoir 31, and the fluid discharge section 35 configured to discharge the solution 10 from the reservoir 31.

Figure 3:
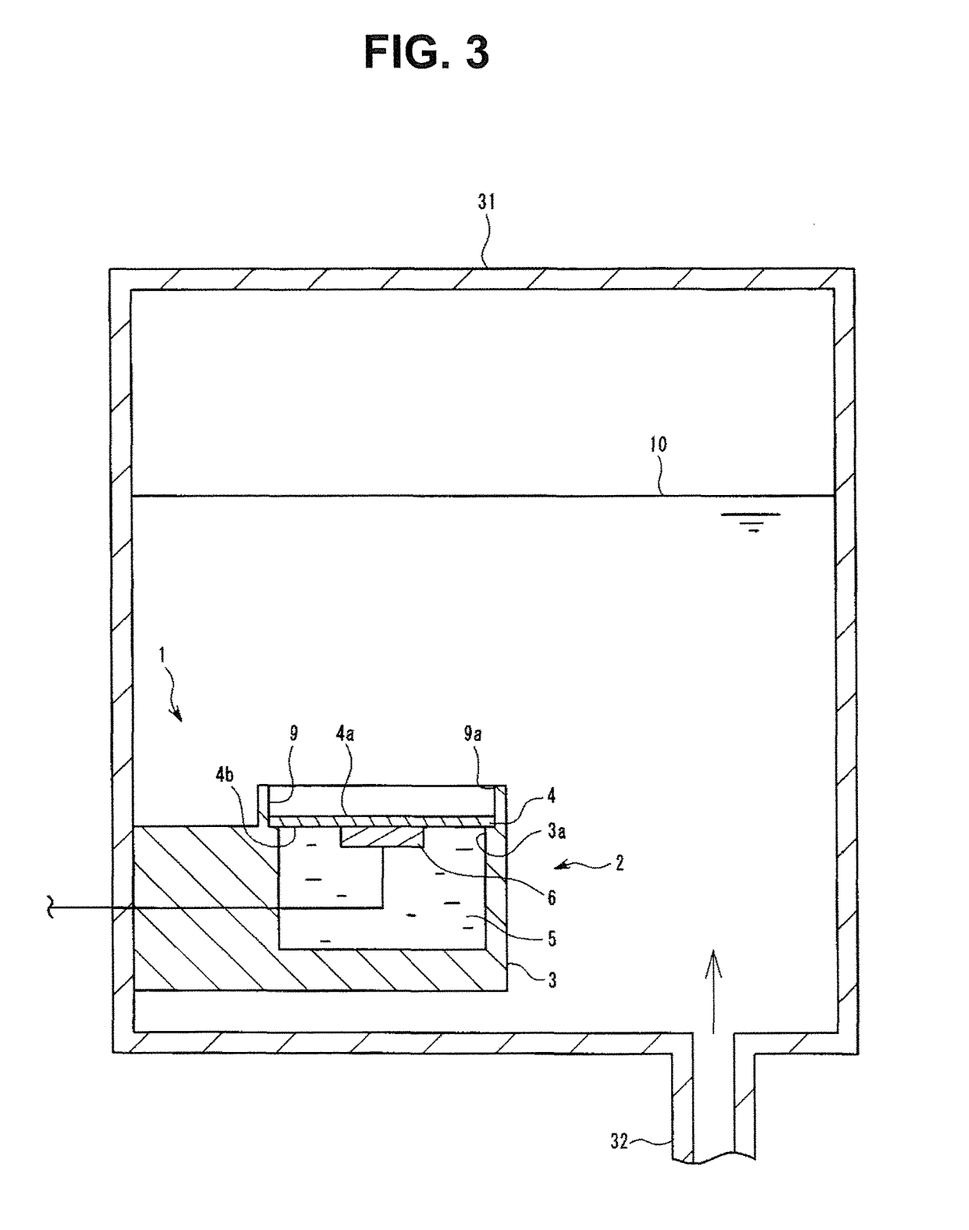
FIG. 3 is a diagram showing a state where a solution is supplied into the reservoir of the first embodiment.

As described above, according to the endoscope reprocessor 20 having the configuration as described above, in the case of measuring the concentration of the solution 10 by the concentration meter 1, the fluid supply section 34 is operated, and the solution 10 is supplied to the reservoir 31. At this time, the volume of the solution to be supplied to the reservoir 31 by the operation of the fluid supply section 34 takes a value according to which the liquid level of the solution 10 in the reservoir 31 reaches above the opening section 9a of the pool section 9, as shown in FIG. 3.

When the opening section 9a is placed below the liquid level of the solution 10, the solution 10 enters the pool section 9, and the first surface 4a of the permeable membrane 4 is immersed in the solution 10. When the first surface 4a of the permeable membrane 4 is immersed in the solution 10, measurement of the concentration of the solution 10 by the concentration meter 1 is enabled.

Figure 4:
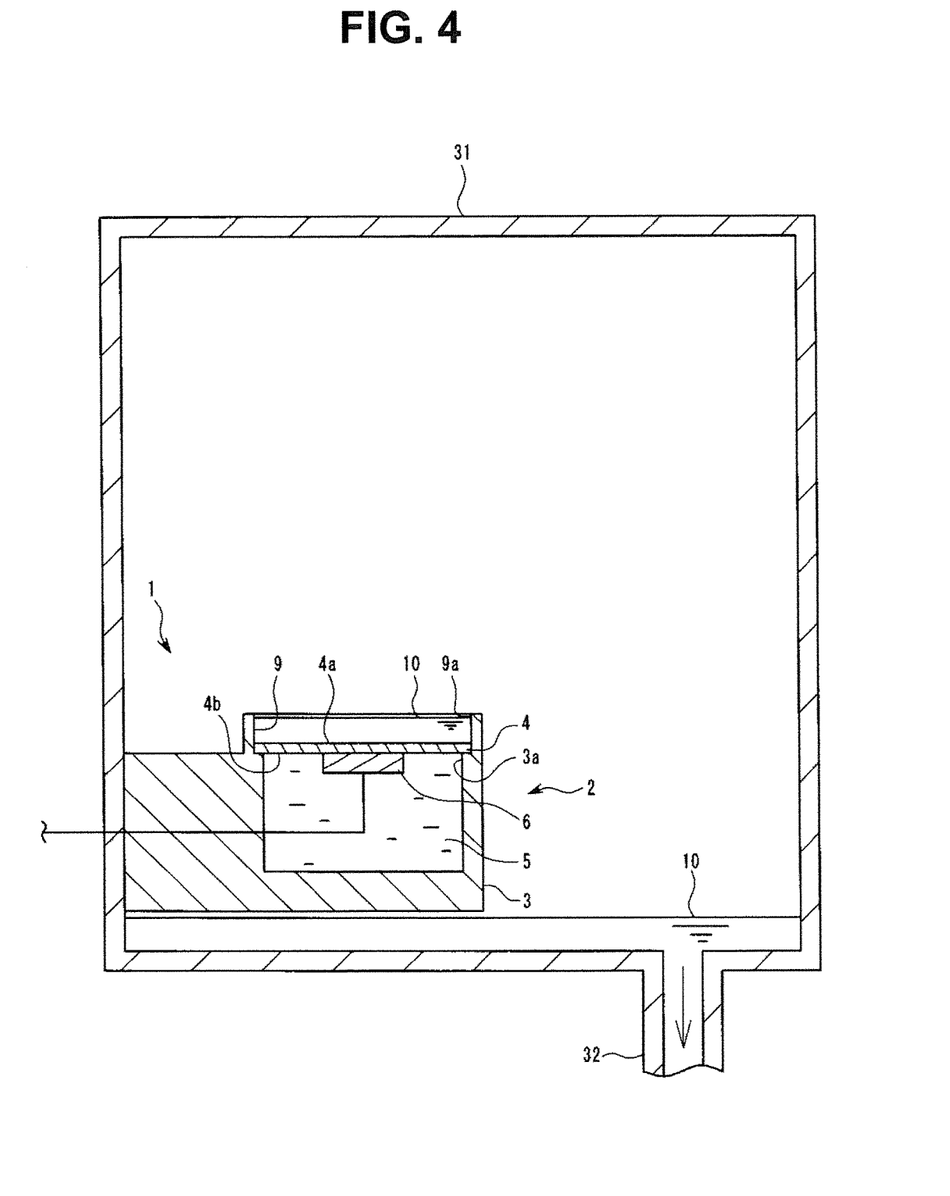
FIG. 4 is a diagram showing a state where the solution is discharged from the reservoir of the first embodiment.

After measurement of the concentration of the solution 10 by the concentration meter 1 is completed, the endoscope reprocessor 20 operates the fluid discharge section 35, and, the solution 10 is discharged from the reservoir 31, as shown in FIG. 4. When the solution 10 is discharged, the sensor section 2 of the concentration meter 1 becomes exposed to the air in the reservoir 31.

At this time, the solution 10 is retained in the recessed pool section 9, as shown in FIG. 4, and thus, a state where the solution 10 is in contact with the first surface 4a of the permeable membrane 4 is maintained even after the fluid is discharged from the reservoir 31.

Accordingly, with the endoscope reprocessor 20 of the present embodiment, the permeable membrane 4 can be maintained in a wet state by the solution 10 even when the sensor section 2 of the concentration meter 1 is exposed to the air in the reservoir 31.

By maintaining the permeable membrane 4 in a wet state by the solution 10, it is enabled to reduce the wait time after the sensor section 2 is exposed to the air from the solution 10 until measurement of the concentration of the solution 10 is enabled again. For example, as described above, the endoscope reprocessor 20 is repeatedly placed in a state where the sensor section 2 is immersed in the solution 10, and a state where the sensor section 2 is exposed to the air, but in the present embodiment, the wait time from immersion of the sensor section 2 in the solution 10 until start of the concentration measurement can be reduced. That is, the present embodiment can reduce the period of time necessary for measuring the concentration of the solution 10, which is a disinfecting solution, and can increase the number of endoscopes which can be subjected to the disinfecting process per unit time period.

Note that the concentration of the solution 10 which is retained in the pool section 9 while the sensor section 2 is exposed to the air may possibly take a value different from that of the concentration of the solution 10 that is supplied to the reservoir 31 for the next concentration measurement, but when the liquid level in the reservoir 31 exceeds the opening section 9a, the solution 10 flows into the pool section 9, and the influence of the difference in the concentration is eliminated. It is, for example, desirable to cause a wall surface near the opening section 9a of the pool section 9 to be made of a mesh which allows a liquid to easily pass through, so that the solution 10 in the pool section 9 can be swiftly replaced when the opening section 9a is immersed in the solution 10. Furthermore, a water level sensor may be provided in the reservoir 31 to reliably check whether the opening section 9a of the pool section 9 is immersed in the solution 10. Moreover, the operation time period of the pump 33 is defined so that the pool section 9 is reliably immersed in the solution 10.

Figure 5:
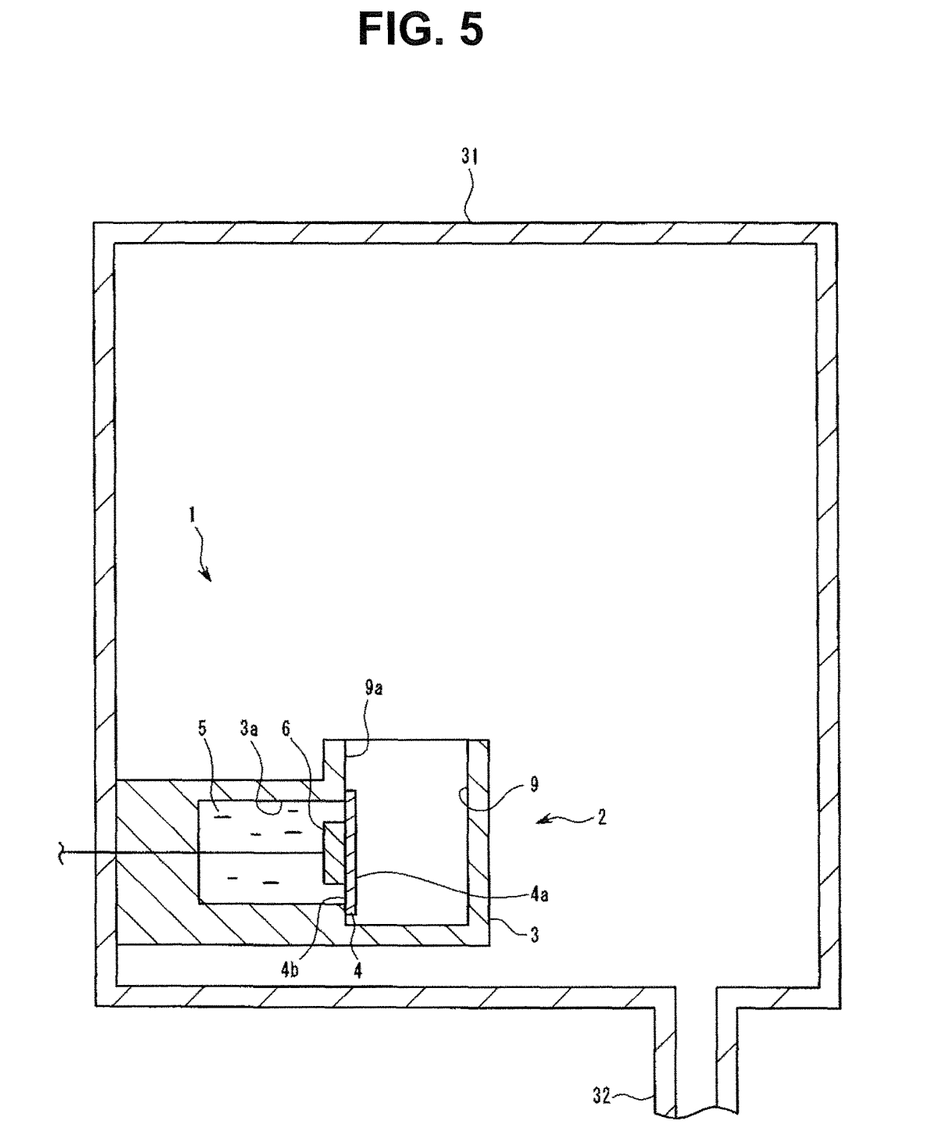
FIG. 5 is a cross-sectional view showing a first modification example of the first embodiment.

FIG. 5 shows a first modification example of the endoscope reprocessor 20. In the present modification example, the first surface 4a of the permeable membrane 4 is exposed in the recessed pool section 9, at a side surface of the pool section 9. In other words, the first surface 4a of the permeable membrane 4 configures a part of the side surface of the pool section 9, and faces the horizontal direction.

Also in the present modification example, the first surface 4a of the permeable membrane 4 comes in contact with the solution 10 retained in the pool section 9, and as in the embodiment described above, the permeable membrane 4 can be maintained in a wet state by the solution 10 for a long period of time even when the sensor section 2 is exposed to the air in the reservoir 31.

Figure 6:
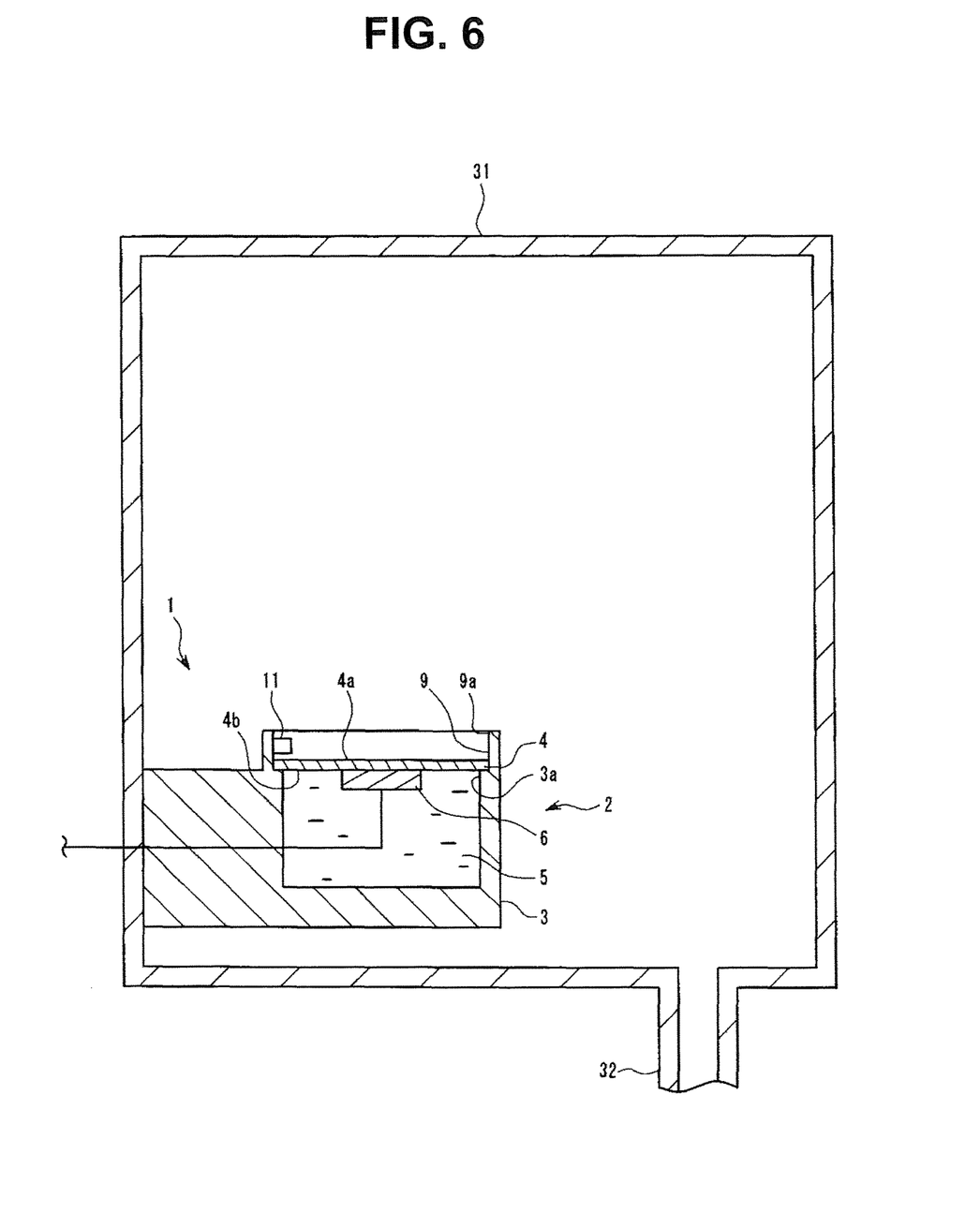
FIG. 6 is a cross-sectional view showing a second modification example of the first embodiment.

FIG. 6 shows a second modification example of the endoscope reprocessor 20. The concentration meter 1 of the present modification example includes a liquid detection sensor 11 configured to detect whether or not the solution 10 is present in the pool section 9. For example, the liquid detection sensor 11 is embodied as a so-called electrode type water level sensor which includes a pair of electrodes that are separated from each other, and which detects whether or not the solution 10 is present in the pool section 9 based on presence/absence of electrical conduction between the pair of electrodes.

The endoscope reprocessor 20 determines whether or not the solution 10 is retained in the pool section 9 when the sensor section 2 is exposed to the air, based on the detection result of the liquid detection sensor 11.

According to the present modification example, the endoscope reprocessor 20 can detect the possibility that the solution 10 is not present in the pool section 9 due to evaporation or shaking of the device and that the permeable membrane 4 is dry.

Second Embodiment

Next, a second embodiment of the present invention will be described. In the following, only the differences from the first embodiment will be described, and the components same as those in the first embodiment will be denoted with the same reference signs, and redundant description will be omitted as appropriate.

Figure 7:
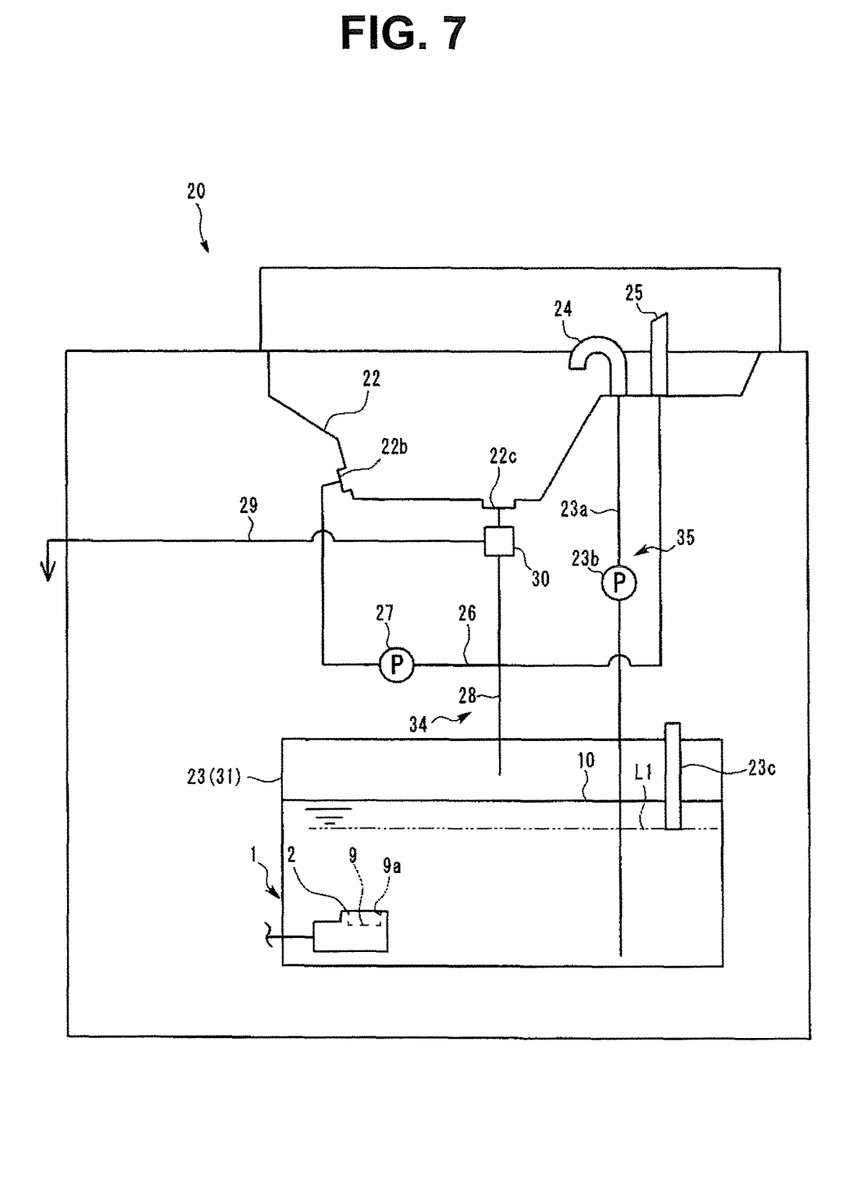
FIG. 7 is a diagram showing a configuration of an endoscope reprocessor of a second embodiment.

An endoscope reprocessor 20 of the present embodiment shown in FIG. 7 is different from the first embodiment in that the sensor section 2 of the concentration meter 1 is provided inside the drug solution tank 23. In the present embodiment, the drug solution tank 23 is the reservoir 31 configured to store the solution 10, and the switching valve 30 and the collection channel 28 are the drug solution supply section 34 configured to supply the solution 10 to the reservoir 31, and the drug solution introduction channel 23a and the drug solution introduction pump 23b are the drug solution discharge section 35.

The endoscope reprocessor 20 according to the present embodiment can, as in the first embodiment, maintain the permeable membrane 4 in a wet state by the solution 10 for a long period of time even if the sensor section 2 of the concentration meter 1 is exposed to the air inside the drug solution tank 23.

By maintaining the permeable membrane 4 in a wet state by the solution 10, it is enabled to reduce the wait time after the sensor section 2 is exposed to the air from the solution 10 until measurement of the concentration of the solution 10 is enabled again. For example, while the endoscope reprocessor 20 is repeatedly placed in a state where the sensor section 2 is immersed in the solution 10 and a state where the sensor section 2 is exposed to the air as described above, the present embodiment can reduce the wait time from immersion of the sensor section 2 in the solution 10 until start of the concentration measurement. That is, the present embodiment can reduce the period of time necessary for measuring the concentration of the solution 10, which is a disinfecting solution, and can increase the number of endoscopes which can be subjected to the disinfecting process per unit time period.

Furthermore, a water level sensor 23c is disposed in the drug solution tank 23, which is the reservoir 31 of the present embodiment. The water level sensor 23c determines whether or not the liquid level of the solution 10 stored in the drug solution tank 23 is above a predetermined water level L1, which is above the opening section 9a of the pool section 9, which is provided to the sensor section 2.

The configuration of the water level sensor 23c is not particularly limited. The water level sensor 23c may be a so-called electrode type water level sensor which includes a pair of electrodes that are separated from each other, and which detects whether or not the liquid level is above the water level L1 based on presence/absence of electrical conduction between the pair of electrodes. Also, for example, the water level sensor 23c may be a so-called float type water level sensor which includes a switch that opens or closes according to vertical fluctuation of a float floating on the solution 10.

The endoscope reprocessor 20 of the present embodiment detects, by the water level sensor 23c, whether or not the liquid level in the drug solution tank 23 is above the predetermined water level L1, before the concentration of the solution 10 is measured by the concentration meter 1. In other words, the endoscope reprocessor 2D determines whether or not the opening section 9a of the pool section 9 of the concentration meter 1 is sunk in the solution 10 before the concentration meter 1, measures the concentration of the solution 10.

When determining that the liquid level in the drug solution tank 23 is above the predetermined water level L1, the endoscope reprocessor 20 carries out measurement of the concentration of the solution 10 by the concentration meter 1.

On the other hand, when determining that the liquid level in the drug solution tank 23 below the predetermined water level L1, the endoscope reprocessor 20 does not carry out measurement of the concentration of the solution 10 by the concentration meter 1, and issues an alarm by emitting sound or light, for example, to notify the user that there is not enough solution 10.

If the liquid level in the drug solution tank 23 is above the predetermined water level L1, the opening section 9a of the pool section 9 of the concentration meter 1 is sunk in the solution 10, and thus, the concentration of the solution 10 stored in the drug solution tank 23 can be reliably measured. However, if the concentration measurement is performed when the liquid level in the drug solution tank 23 is below the predetermined water level L1, it is not certain whether the opening section 9a of the pool section 9 of the concentration meter 1 is sunk in the solution 10 or not, and thus, the measurement result possibly indicates the concentration of the solution 10 which was retained in the pool section 9 when the sensor section 2 was exposed to the air. In the present embodiment, the concentration measurement is not performed in such a case, and thus, the concentration of the solution 10 which was retained in the pool section 9 when the sensor section 2 was exposed to the air can be prevented from being acquired as the measurement result.

Note that the water level sensor 23c may also be used to determine whether or not a volume of solution 10 sufficient to perform a disinfecting process in the processing tank 22 is stored in the drug solution tank 23.

Third Embodiment

Next, a third embodiment of the present invention will be described. In the following, only the differences from the first and the second embodiments will be described, and the components same as those in the first and the second embodiments will be denoted with the same reference signs, and redundant description will be omitted as appropriate.

Figure 8:
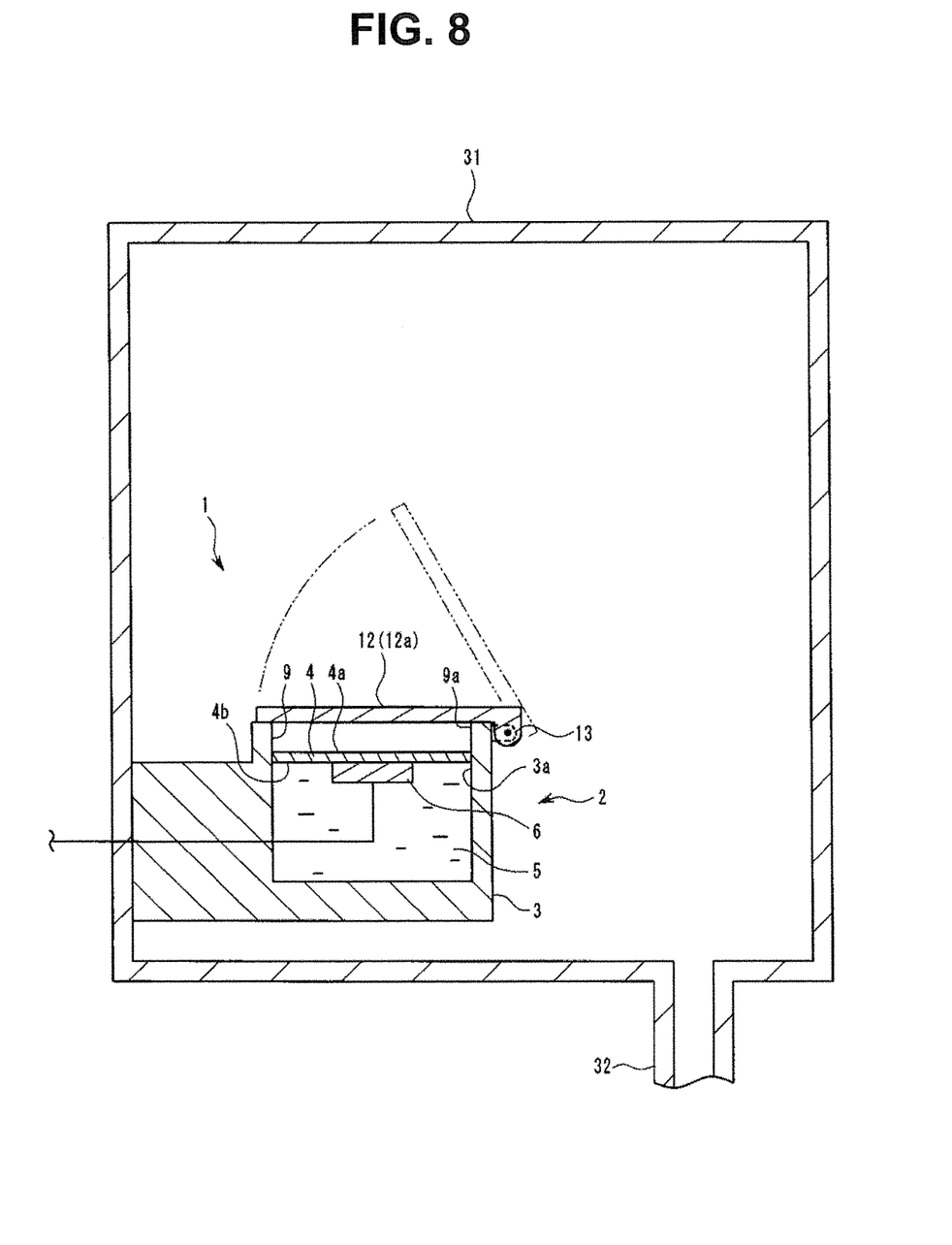
FIG. 8 is a cross-sectional view of a reservoir and a sensor section of a concentration meter of an endoscope reprocessor of a third embodiment.

As shown in FIG. 8, an endoscope reprocessor 20 of the present embodiment includes, inside the reservoir 31, a lid section 12 and a guide section 13. Note that the reservoir 31 may be a container different from the drug solution tank 23 as in the first embodiment, or may be a container the same as the drug solution tank 23 as in the second embodiment.

The lid section 12 is a member configured to open and close the opening section 9a of the pool section 9 of the concentration meter 1. The lid section 12 is capable of moving between a closed position of blocking or narrowing the opening section 9a and an open position of opening the opening section 9a to the space in the reservoir 31. The movement direction and the movement range of the lid section 12 are defined by the guide section 13 having a confituration such as a guide rail or a hinge. Note that the guide section 13 may be provided on an inner wall surface of the reservoir 31, instead of being provided to the main body section 3 of the sensor section 2 as in the present embodiment as illustrated.

The lid section 12 includes a float section 12a with a lower specific gravity than the solution 10 and a higher specific gravity than air. When the liquid level of the solution 10 in the reservoir 31 is above the opening section 9a of the pool section 9, the lid section 12 is moved to the open position by the buoyancy of the float section 12a in the solution 10.

On the other hand, when the liquid level of the solution 10 in the reservoir 31 is below the opening section 9a of the pool section 9, the lid section 12 is moved to the closed position. The force for moving the lid section 12 to the closed position may be due to the weight of the lid section and the float section 12a, or due to a spring mechanism. Note that in the case of using a spring mechanism, the force of the spring for moving the lid section 12 to the closed position is smaller than the force for moving the lid section 12 to the open position generated by the buoyancy of the float section 12a in the solution 10.

More specifically, in the present embodiment shown in FIG. 8, the lid section 12 is disposed in a manner capable of rotating with respect to the main body section 3 of the sensor section 2, by the hinge-shaped guide section 13. The lid section 12 is a plate-shaped member, and when the lid section 12 is at the closed position, the opening section 9a of the pool section 9 is blocked or narrowed. The open position of the lid section 12 according to the present embodiment is the position reached by the lid section 12 rotating upward from the closed position, in the direction away from the opening section 9a.

Furthermore, the lid section 12 is configured by a material with a lower specific gravity than the solution 10 and a higher specific gravity than the air. That is, in the present embodiment, the entire lid section 12 functions as the float section 12a. Note that the float section 12a may be integrally formed with the lid member 12 as in the present embodiment, or may be a member separate from the lid member 12, which is coupled to the lid member 12 via a coupling member such as a chain or a string.

Figure 9:
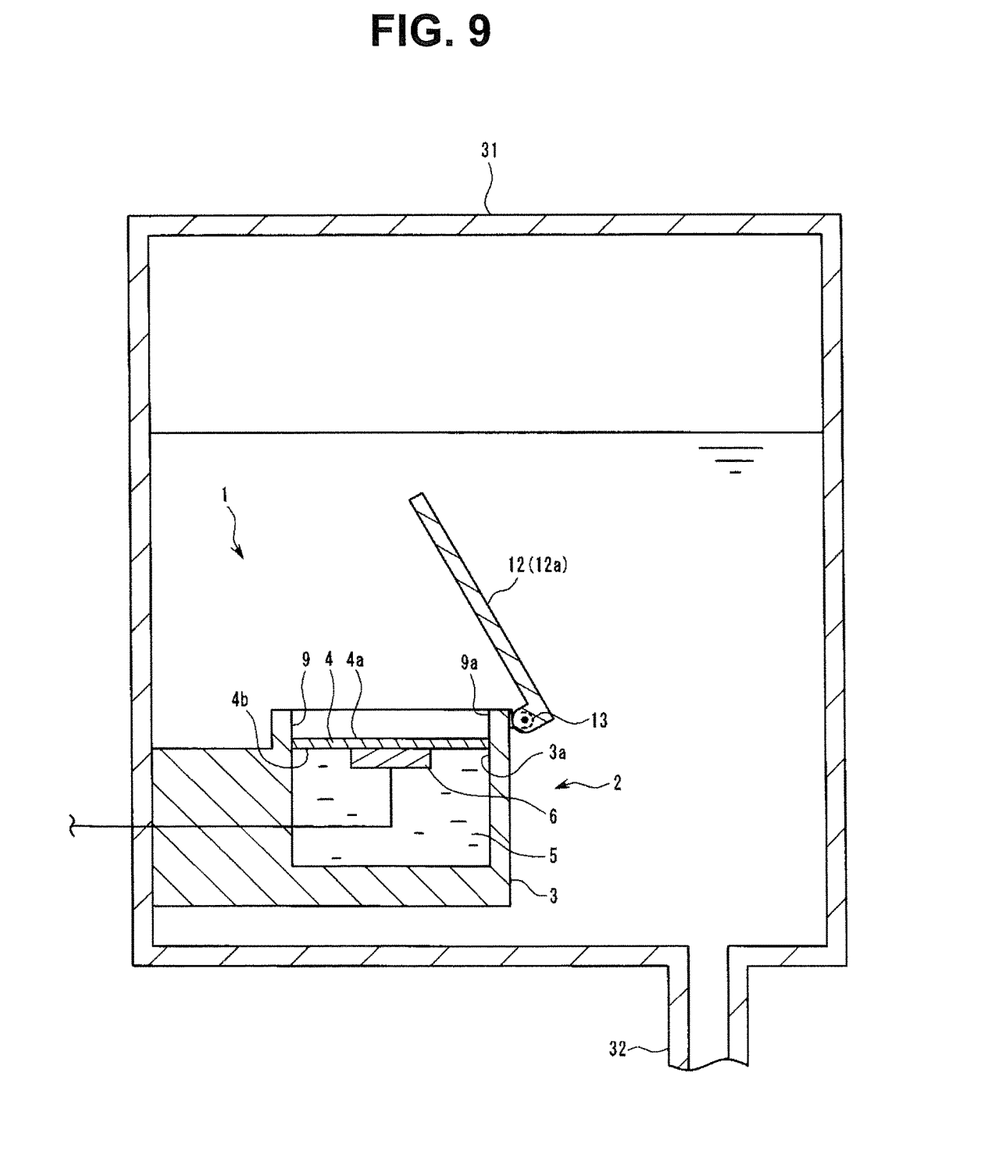
FIG. 9 is a diagram showing a state where a solution is supplied into the reservoir of the third embodiment.

When the liquid level of the solution 10 in the reservoir 31 is below the opening section 9a of the pool section 9, the lid section 12 is exposed to the air, and is positioned at the closed position by the weight of the lid section 12, as shown in FIG. 8. On the other hand, as shown in FIG. 9, when the liquid level of the solution 10 in the reservoir 31 is above the opening section 9a of the pool section 9, the lid section 12 is moved to the open position by buoyancy.

According to the endoscope reprocessor 20 of the present embodiment configured in the above manner, when the sensor section 2 of the concentration meter 1 is exposed to the air in the reservoir 31, the opening section 9a of the pool section 9 is blocked or narrowed by the lid member 12, and thus, evaporation of the solution 10 retained in the pool section 9 can be prevented or suppressed, and the permeable membrane 4 can be maintained in a wet state for a longer period of time than in the first and the second embodiments.

Figure 10:
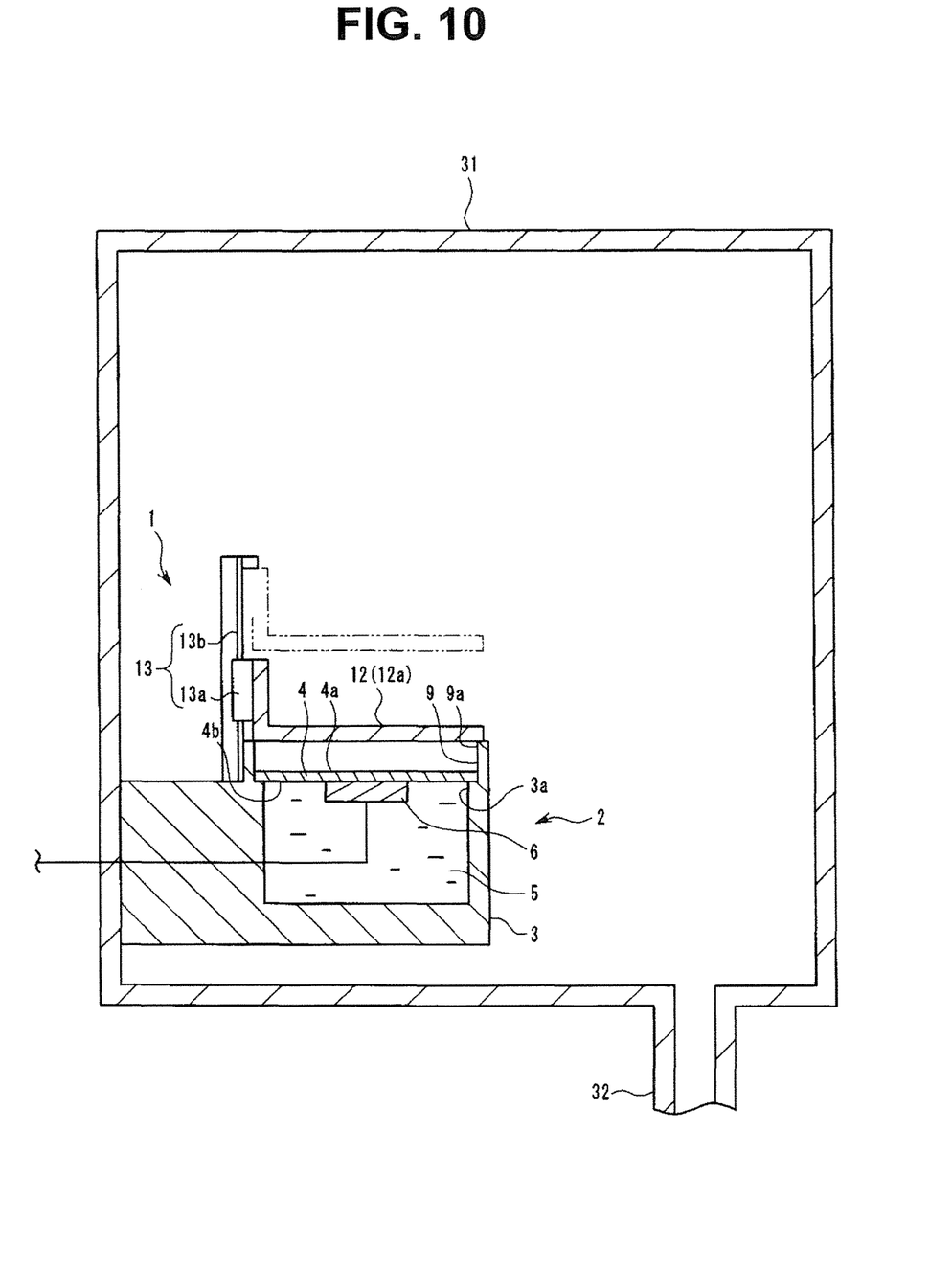
FIG. 10 is a cross-sectional view of a first modification example of the third embodiment.

FIG. 10 shows a first modification example of the endoscope reprocessor 20 of the present embodiment. In the present modification example, the guide section 13 configured to guide movement of the lid section 12 is embodied as a guide rail. The guide section 13 is configured from a slide section 13a to which the lid section 12 is fixed, and a rail section 13b on which the slide section 13a slides. The rail section 13b guides the slide section 13a to move in the vertical direction. Note that the rail section 13b may be fixed to the main body section 3 as shown in the drawing, or may be fixed to an inner wall surface of the reservoir 31.

In the present modification example, when the liquid level of the solution 10 in the reservoir 31 is below the opening section 9a of the pool section 9, the lid section 12 is exposed to the air and is positioned at the closed position below by the weight of the lid section 12. On the other hand, when the liquid level of the solution 10 in the reservoir 31 is above the opening section 9a of the pool section 9, the lid section 12 is moved to the open position above by buoyancy.

Figure 11:
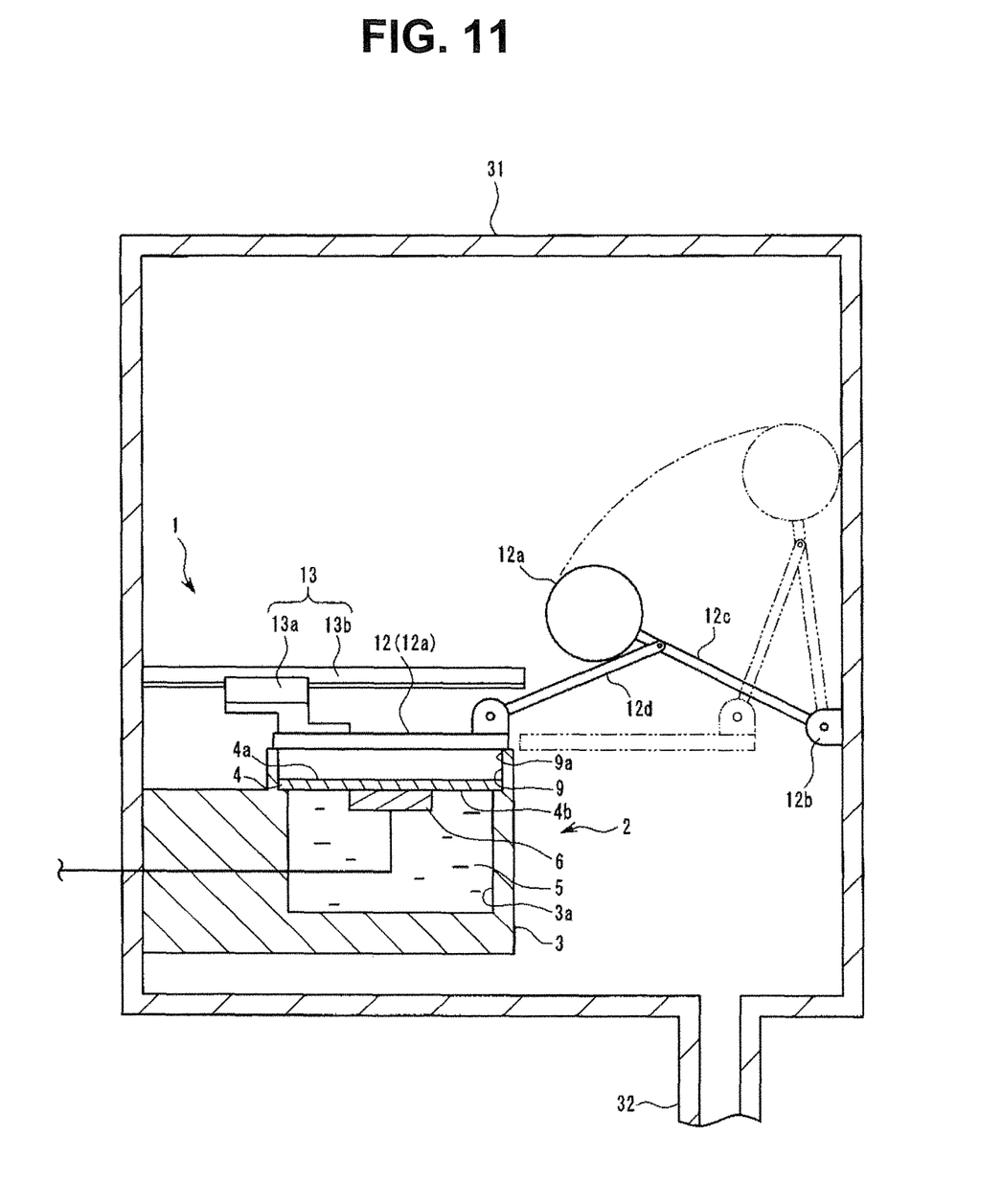
FIG. 11 is a cross-sectional view of a second modification example of the third embodiment.

FIG. 11 shows a second modification example of the endoscope reprocessor 20 of the present embodiment. In the present modification example, the guide section 13 configured to guide movement of the lid section 12 is embodied as a guide rail. The guide section 13 is configured from the slide section 13a to which the lid section 12 is fixed, and the rail section 13b on which the slide section 13a slides. The rail section 13b guides the slide section 13a to move in the horizontal direction.

The lid section 12 moves forward and backward in the horizontal direction, between the closed position above the opening section 9a of the pool section 9 and the open position retracted from above the opening section 9a. Note that the rail section 13b may be fixed to an inner wall surface of the reservoir 31 as shown in the drawing, or may be fixed to the main body section 3.

In the present modification example, the float section 12a is a member separate from the lid section 12. The float section 12a is fixed to a distal end of an arm section 12c having a base section 12b provided on an inner wall surface of the reservoir 31 as the proximal end. The arm section 12c swings around a horizontal rotation shaft at the base section 12b. That is, the arm section 12c swings in the vertical direction. The rotation shaft of the arm section 12c is orthogonal to the extending direction of the rail section 13b when seen from vertically above. In a state where the arm section 12c is at the lowest position, the float section 12a is at a predetermined height higher than the opening section 9a of the pool section 9. Note that the base section 13b may be provided to the main body section 3.

The arm section 12c is coupled to the lid section 12 by a link member 12d. Swinging of the arm section 12c is transmitted to the lid section 12 by the link member 12d. The lid section 12 moves in the direction from the closed position to the open position in coordination with the upward swinging of the arm section 12c. Also, the lid section 12 moves in the direction from the open position to the closed position in coordination with the downward swinging of the arm section 12c.

In the present modification example, when the liquid level of the solution 10 in the reservoir 31 is below the opening section 9a of the pool section 9, the arm section 12c including the float section 12a swings downward, and thus, the lid section 12 is positioned at the closed position. On the other hand, when the liquid level of the solution 10 in the reservoir 31 is above a predetermined height above the opening section 9a of the pool section 9, the arm section 12c including the float section 12a swings upward due to the buoyancy, and the lid section 12 is moved to the open position.

Note that the present invention is not limited to the embodiments described above, and may be changed as appropriate within the scope or the spirit of the invention indicated by the appended claims and the entire specification, and an endoscope reprocessor obtained by such a change is also within the technical scope of the present invention.

What is claimed is:

1. An endoscope reprocessor comprising:
   a reservoir configured to store a solution;
   a fluid supply section configured to supply the solution into the reservoir;
   a fluid discharge section configured to discharge the solution from the reservoir;
   a recessed pool section that is fixed inside the reservoir and having a bottom surface positioned below an opening section in a gravitational direction; and
   a concentration meter including
      a permeable membrane having a first surface exposed inside the pool section, at least a part of the first surface being positioned below the opening section in the gravitational direction,
      an accommodation section having a container shape and including a part of a second surface of the permeable membrane as an inner surface, the second surface being on an opposite side to the first surface,
      internal liquid that is accommodated in the accommodation section, and
      an electrode that is accommodated in the accommodation section.

2. The endoscope reprocessor according to claim 1, comprising:
   a float section that is disposed in the reservoir in a manner capable of moving vertically in the gravitational direction, the float section having a lower specific gravity than the solution and a higher specific gravity than air; and
   a lid section configured to move in coordination with vertical fluctuation of the float section, the lid section blocking or narrowing the opening section when a liquid level of the solution in the reservoir is below the opening section of the pool section in the gravitational direction, the lid section opening the opening section when the liquid level of the solution in the reservoir is above the opening section of the pool section in the gravitational direction.

* * * * *